United States Patent [19]
Okamoto et al.
[11] Patent Number: 4,567,298
[45] Date of Patent: Jan. 28, 1986

[54] POLY(DIPROPARGYLAMINE) AND DERIVATIVES THEREOF PER SE AND P-DOPED AND PROCESSES FOR PREPARING SAME

[75] Inventors: Yoshiyuki Okamoto, Fort Lee, N.J.; Edward F. Hwang, Brooklyn, N.Y.

[73] Assignee: W. R. Grace & Co., New York, N.Y.

[21] Appl. No.: 639,457

[22] Filed: Aug. 10, 1984

Related U.S. Application Data

[62] Division of Ser. No. 579,407, Feb. 13, 1984, Pat. No. 4,497,727.

[51] Int. Cl.[4] .......................................... C07C 103/127
[52] U.S. Cl. .................................................... 564/215
[58] Field of Search .......................................... 564/215

[56] References Cited

U.S. PATENT DOCUMENTS 4,201,725 5/1980 Pigerol et al. .................. 564/215 X

*Primary Examiner*—Paul F. Shaver
*Attorney, Agent, or Firm*—Richard P. Plunkett

[57] ABSTRACT

This invention relates to novel polymers of dipropargylamine and derivatives thereof, a process for preparing same and the electrically conductive polymers resulting from doping poly(dipropargylamine) and derivatives thereof.

1 Claim, No Drawings

POLY(DIPROPARGYLAMINE) AND DERIVATIVES THEREOF PER SE AND P-DOPED AND PROCESSES FOR PREPARING SAME

BACKGROUND OF THE INVENTION

This is a division of application Ser. No. 579,,407 filed Feb. 13, 1984, now U.S. Pat. No. 4,497,727.

1. Field of the Invention

This invention relates to novel polymers of dipropargylamine and derivatives thereof. Additionally, the invention relates to a process for preparing polymers of dipropargylamine and derivatives thereof. Further, this invention relates to electrically conductive polymers resulting from doping poly(dipropargylamine) and derivatives thereof and a process therefor.

2. Description of the Prior Art

Various terminal, diacetylenic monomers of the formula, i.e.,:

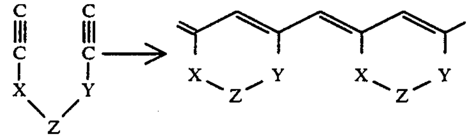

wherein X and Y=CO and Z=O and X and Y=$CH_2$ and Z=$CH_2$ or O when polymerized with a suitable catalyst yield six-membered cyclic conjugated polymers. See (1) H. W. Gibson, F. C. Bailey, A. J. Epstein, H. Rommelmann and J. M. Pochan, JCS, Chem. Comm., 426 (1980); (2) H. W. Gibson and J. M. Pochan, Proc. Macromolecular, Symp., IUPAC, Amherst, MA, July 1982, p. 406; (3) J. K. Stille and D. A. Frey, J. Am. Chem. Soc., 83, 1697 (1961); and (4) L. A. Akopyan, G. V. Ambartsumyan, E. V. Ovakimyan and S. G. Matsoyan, Chemical Abstracts, 8b, 2 (1977). The resulting polymers were found to be highly conductive upon doping with $I_2$ and $AsF_5$.

OBJECTS OF THE INVENTION

One object of the invention is to produce polymers of dipropargylamine and derivatives thereof. Another object of the invention is to provide a polymerization procedure, in accordance with the proceeding objects, using a novel catalyst system. Yet another object of the instant invention, in accordance with the proceeding objects, is to provide a procedure whereby the polymers of dipropargylamine and derivatives thereof are made electrically conductive. Other objects will become apparent from a reading hereinafter.

DESCRIPTION OF THE INVENTION

Dipropargylamine and derivatives thereof of the formula:

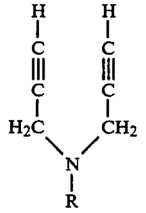

wherein R is H, $C_2H_5$, $(CH_3)_3C$ and

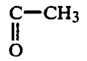

are polymerized in an inert atmosphere either (1) by heating at a temperature in the range 150° to 185° C. or (2) in an organic diluent containing a catalytic amount of $PdCl_2$ or $WCl_6$, said diluent having a refluxing temperature in the range 50° to 120° C. The resulting polymers, all hereinafter for the sake of brevity being referred to as dipropargylamine polymers, contain recurring structural units of the formula:

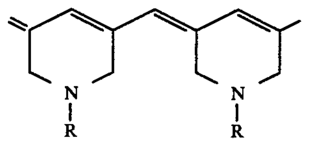

wherein R is as aforestated.

The polymerization catalyst is present in an amount ranging from 0.25 to 2% by weight of the monomer being polymerized.

Organic diluents employed in the polymerization having refluxing temperatures in the range 50° to 120° C. include, but are not limited to, pyridine, benzene, toluene and hexane.

The polymers have a weight average molecular weight in the range 5,000 to 10,000. The dipropargylamine polymers can be made electrically conductive by p-doping using conventional methods.

A wide variety of doping materials may suitably be employed in doping the dipropargylamine polymers to effectively modify its room temperature electrical conductivity. Since the conductivity of the starting dipropargylamine polymers will be relatively low to begin with, i.e., on the order of about $10^{-10}$ to $10^{-14}ohm^{-1}cm^{-1}$, the required modification for most practical applications will be to effect an increase in conductivity. Dopants suitable for effecting an increase in the room temperature p-type electrical conductivity of the dipropargylamine polymers starting material are electron acceptor dopants, including, for example, $Br_2$, $I_2$, ICl, IBr, $AsF_5$, $Cl_2$, HBr, $BF_3$, $BCl_3$, $SO_2$, $SO_3$, $SO_2Cl_2$, $POF_3$, $NO_2$, HCN, ICN, $O_2$, $SiF_4$, NO, tetracyanoquinodimethane (TCNQ) and transition metal carbonyl, phosphine and olefin derivatives. Each of these electron acceptor dopants will effect an increase, to varying degrees, in the room temperature p-type electrical conductivity of the dipropargylamine polymers starting material.

The extent to which any given electron acceptor dopant will increase the conductivity of the dipropargylamine polymer will depend upon the degree of doping up to a certain point at which the maximum conductivity is obtained for that dopant. Such maximum conductivity will generally be obtained at a degree of doping not greater than about 0.50 mole of electron acceptor dopant per mole of monomer unit. The highest room temperature p-type electrical conductivity thus far achieved in accordance with the present invention, i.e., $10^{-3}ohm^{-1}cm^{-1}$, was obtained with iodine doped dipropar gylamine polymers containing about 0.5 mole of iodine per mole of monomer unit.

In carrying out the method of the present invention for producing a p-type doped dipropargylamine polymers, the polymers are contacted with a dopant, which may be either in the vapor phase or in solution, whereby uptake of the dopant into the dipropargylamine polymer molecules occurs to a degree proportional to the dopant concentration and the contacting period. The contacting period is controlled so that the corresponding degree of doping will be such as to provide the resulting doped dipropargylamine polymer with p-type electrical conductivity. For example, with the preferred electron acceptor dopants in accordance with the present invention, e.g., iodine, the starting dipropargylamine polymer may be contacted in vacuum with the vapor of the electron acceptor dopant for a contacting period ranging from a few seconds to about 24 hours to provide a degree of doping within the range of from less than 0.10 to 0.50 moles of electron acceptor dopant per mole of monomer unit and thereby provide the doped dipropargylamine polymer with room temperature p-type electrical conductivity within the range of from about $10^{-7}$ to $10^{-3}$ $ohm^{-1}cm^{-1}$.

A preferred doping procedure is to fill a vessel with powdered polymer to be doped. The vessel is then evacuated, and the vapor of the dopant is then allowed to enter the vessel.

The doping procedure may also be carried out by placing the starting dipropargylamine polymer powder in a solution of the dopant, i.e., TCNQ or iodine, in an appropriate organic solvent inert to the dipropargylamine polymer, such as, for example, benzene, cyclohexane, tetrahydrofuran or the like. By trial and error, it is found what length of time is necessary to leave the dipropargylamine polymer in the solution to obtain the desired degree of doping. At the completion of the doping period, the doped polymers are removed from the doping solution and rinsed in an additional amount of the organic solvent to remove any residual doping solution therefrom, and the excess solvent is then pumped off in a high vacuum.

Thermogravimetric analysis of polymers were carried out on a Dupont Thermal Analyzer, Model 1090. Samples were preheated and cooled at room temperature in a desiccator prior to analysis. Electrical conductivity of the polymers was measured on pellets compressed under 50 atm pressure using two nickel electrodes with a Keithley Electrometer (610 A).

The following examples will aid in explaining, but expressly not limit, the instant invention. Unless otherwise noted, all parts and percentages are by weight.

EXAMPLE 1

Preparation of Dipropargyl-t-butylamine

A mixture of 0.15 mole of t-butylamine, 0.35 mole of anhydrous, powdered potassium carbonate and 250 moles of ether was stirred mechanically and 0.25 mole of propargylbromide was added dropwise. The mixture was refluxed for about 10 hours. Water was added to dissolve the salt. The ether layer was separated and the aqueous layer was extracted twice with ether. The combined ether solution was dried over anhydrous $MgSO_4$. The dipropargyl-t-butylamine produced was distilled at 63°-65° C./20 mm Hg to yield a yellowish liquid in a 45% yield: IR 3300, 3100, 2980 and 2940 $cm^{-1}$; NMR ($CDCl_3$)δ1.10, 2.20 and 3.45.

EXAMPLE 2

Preparation of Dipropargylethylamine

Propargyl bromide (0.75 mole) was added dropwise with stirring to 1 mole of 70% aqueous solution of ethylamine while maintaining the temperature at 35°-45° C. for 5-8 hours. After slow cooling to room temperature, 1.1 mole of sodium hydroxide solution was added dropwise with stirring over a 1 hour period. The layers were separated, the aqueous portion was extracted with ether and the extract was combined with the amine layer. The ethereal solution was dried over anhydrous potassium carbonate and fractionally distilled at 84°-87° C./65 mm Hg. to obtain a yellowish liquid, yield 45%; IR 3300, 2950-2980; 2120 $cm^{-1}$; NMR ($CDCl_3$)δ, 0.88-1.25, 2.20-2.70, 3.20-3.40.

EXAMPLE 3

Preparation of Dipropargylacetamide

Acetyl chloride (0.1 mole) was added dropwise into the chloroform solution containing triethylamine (0.15 mole) and 0.1 mole of purified N,N-dipropargylamine with constant stirring. The precipitate was separated by filtration and the chloroform solution was washed twice with water. The solution was then dried over anhydrous potassium carbonate. The dipropargylacetamide produced was distilled (b.p. 80°-82° C./15 mm Hg) and obtained in 80% yield. IR 3300, 3100, 2990 and 1650 $cm^{-1}$: NMR(neat/TMS)δ2.0, 2.45-2.60 and 4.0-4.1.

EXAMPLE 4

Polymerization of dipropargylamine

Dipropargylamine (5.0 g), commercially available from Aldrich Chemical Co., and purified by distillation, b. p. 62°-65° C./11 mm Hg. were sealed in a glass tube and heated at 175° C. for 4 days. A black, solid polymer product having a melting point in excess of 360° C. with no acetylene bond absorption at 2100 $cm^{-1}$ was obtained in quantitative yield. The product was not soluble in methylene chloride, tetrahydrofuran, pyridine or trifluoroacetic acid.

EXAMPLE 5

Dipropargylamine (3.0 g), commercially available from Aldrich Chemical Co., and purified by distillation, b. p. 62°-65° C./11 mm Hg. were admixed with 1% by weight of the monomer of $PdCl_2$ catalyst and 40 ml pyridine. The admixture was refluxed for 2 hours. The resultant dipropargylamine polymer product was obtained as a black solid having a melting point in excess of 360° C. in a 50% yield. The product was slightly soluble in pyridine and contained no acetylene bond absorption.

EXAMPLE 6

Example 4 was repeated except that 5.0 g of dipropargyl-t-butylamine from Example 1 was substituted for the dipropargylamine. A black, solid product in quantitative yield was obtained. The polymer product was soluble in pyridine and methylene chloride and decomposed at 230° C.

EXAMPLE 7

Example 5 was repeated except that 5.0 g of dipropargyl-t-butylamine was substituted for the dipropargylamine. The resultant dipropargyl-t-butylamine polymer was obtained in a 45% yield. The polymer was soluble in pyridine, tetrahydrofuran and methylene chloride. The polymer decomposed at 170° C.

EXAMPLE 8

Example 4 was repeated except that 5.0 g of dipropargylethylamine was substituted for the dipropargylamine. The resultant dipropargylethylamine polymer was obtained as a brown solid in an 80% yield. The polymer was soluble in pyridine.

EXAMPLE 9

Example 5 was repeated except that 5.0 g of dipropargylethylamine was substituted for the dipropragylamine. The resultant dipropargylethylamine polymer product was obtained as a brown solid in a 40% yield.

EXAMPLE 10

Example 4 was repeated except that 5.0 g of dipropargylacetamide from Example 3 was substituted for the dipropargylamine. The resultant dipropargylacetamide polymer product was obtained as a black, shiny solid in a quantitative yield having a melting point in excess of 360° C. The polymer product was soluble in pyridine and tetrahydrofuran and contained no acetylene bond absorption.

EXAMPLE 11

Example 5 was repeated except that 5.0 g of dipropargylacetamide from Example 3 was substituted for the dipropargylamine. The resultant dipropargylacetamide polymer product was obtained as a black solid in a 40–50% yield. The polymer product had a melting point in excess of 360° C. and was soluble in pyridine and methylene chloride.

EXAMPLE 12

Example 5 was repeated except that 5.0 g of dipropargylethylamine was substituted for the dipropargylamine, 1% by weight of the monomer of $WCl_6$ was used as the catalyst, and 40 ml of benzene was substituted for the pyridine. The admixture was refluxed for 2 hours. The resultant dipropargylethylamine polymer product was obtained as a brown solid in a 10% yield.

Various of the polymers from Examples 4–12 were p-doped and measured for electrical conductivity. Charge transfer complexes of the dipropargylamine polymers with tetracyanoquinodimethane (TCNQ) were prepared by stirring a mixture of a weight amount of the polymer and TCNQ in tetrahydrofuran at room temperature for several hours. The complex obtained was filtered, washed with methanol and dried under reduced pressure. The conductivity of the complex (0.5:1 mole ratio of TCNQ to the monomer unit) is set out in TABLE I. Additionally shown in TABLE I is the electrical conductivity when the dipropargylamine polymers were p-doped with $I_2$. Crystals of $I_2$ were placed in a desiccator along with a weighed amount of the polymer and left to stand for several days. The results of the $I_2$ doping are also shown in TABLE I:

TABLE I

Electrical Conductivities of Polymers

| Polymer/Polymerization Condition | Dopant | Electrical Conductivity ($ohm^{-1}cm^{-1}$ at 25° C.) |
|---|---|---|
| Dipropargyl-t-butylamine | — | $10^{-14}$ – $10^{-12}$ |
| (thermal) | $I_2$ | $10^{-6}$ |
| | TCNQ | $10^{-7}$ |
| ($PdCl_2$ catalyst) | — | $10^{-12}$ |
| | TCNQ | $10^{-5}$ |
| | $I_2$ | $10^{-7}$ |
| Dipropargylamine polymer | — | $10^{-12}$ |
| (thermal) | $I_2$ | $10^{-6}$ |
| | TCNQ | $10^{-6}$ |
| ($PdCl_2$ catalyst) | — | $10^{-12}$ |
| | TCNQ | $10^{-5}$ |
| | $I_2$ | $10^{-4}$ |
| Dipropargylacetamide | — | $10^{-10}$ |
| (thermal) | $I_2$ | $10^{-4}$ |
| | TCNQ | $10^{-7}$ |
| ($PdCl_2$ catalyst) | — | $10^{-13}$ |
| | TCNQ | $10^{-4}$ |
| | $I_2$ | $10^{-6}$ |
| Dipropargylethylamine | — | $10^{-14}$ |
| (thermal) | $I_2$ | $10^{-5}$ |
| | TCNQ | $10^{-5}$ |
| ($PdCl_2$ catalyst) | — | $10^{-13}$ |
| | TCNQ | $10^{-4}$ |
| | $I_2$ | $10^{-3}$ |
| $WCl_6$ catalyst | $I_2$ | $10^{-5}$ |

We claim:

1. A compound of the formula:

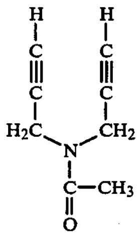

* * * * *